United States Patent [19]

Anderson et al.

[11] 4,207,264

[45] Jun. 10, 1980

[54] REARRANGEMENT OF ARALKYL HYDROPEROXIDES TO FORM PHENOLS AND CARBONYL COMPOUNDS

[75] Inventors: John E. Anderson; Ernest G. Hildenbrand, both of Houston, Tex.

[73] Assignee: The Goodyear Tire & Rubber Company, Akron, Ohio

[21] Appl. No.: 345,342

[22] Filed: Mar. 27, 1973

Related U.S. Application Data

[63] Continuation of Ser. No. 872,009, Oct. 29, 1969, abandoned.

[51] Int. Cl.$^2$ .............................................. C07C 45/00
[52] U.S. Cl. .................................... 568/385; 568/768; 568/781; 568/766; 568/798
[58] Field of Search ............... 260/593 A, 619 R, 598, 260/586, 625, 621 C, 601

[56] References Cited

U.S. PATENT DOCUMENTS

| | | | |
|---|---|---|---|
| 2,842,597 | 7/1958 | Pacout et al. | 260/593 A |
| 3,271,457 | 9/1966 | Bewley et al. | 260/593 A |
| 3,497,561 | 6/1967 | Gelbein et al. | 260/593 A |

FOREIGN PATENT DOCUMENTS

| | | | |
|---|---|---|---|
| 522886 | 3/1956 | France | 260/593 |
| 1202687 | 8/1970 | United Kingdom. | |

OTHER PUBLICATIONS

Frid; Chem. Abst. 75, 98267p (Khim. Prom. 1971, 47(7) pp. 492-494).
Copatin et al.; Chem. Abst. 68; 79971c (Khim. Prom. 43(9) pp. 671-673 (1967)).

*Primary Examiner*—James O. Thomas, Jr.
*Assistant Examiner*—James H. Reamer
*Attorney, Agent, or Firm*—Browning, Bushman & Zamecki

[57] ABSTRACT

A continuous process for cleaving aralkyl hydroperoxides in acid media to yield phenols and carbonyl compounds in a reactor arranged and operated to limit the total residence time to less than the time required to form discoloration products.

8 Claims, 2 Drawing Figures

REARRANGEMENT OF ARALKYL HYDROPEROXIDES TO FORM PHENOLS AND CARBONYL COMPOUNDS

This application is a continuation of application Ser. No. 872,009, filed Oct. 29, 1969 now abandoned.

BACKGROUND OF THE INVENTION

It is well known that aralkyl hydroperoxides can be subjected to a cleavage reaction in the presence of an acid catalyst to yield phenols and carbonyl compounds.

This type of reaction is generally applicable to aralkyl hydroperoxides of the form:

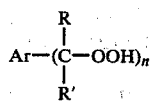

where: Ar is a benzene nucleus, substituted benzene, alkyl benzene or polynuclear aromatic, R and R' are hydrogen, alkyl groups or cycloalkyl groups, and n is a whole number from 1 to 6.

Numerous methods for performing the catalytic cleavage of aralkyl hydroperoxides have been disclosed in the patent literature. These methods comprise the use of many different catalysts such as sulfuric acid, other strong mineral acids, and Lewis acids, e.g. boron trifluoride, aluminum chloride, etc. For examples of the range of catalysts employed in this cleavage reaction see U.S. Pat. Nos. 3,376,352; 2,718,172; 2,626,281; 3,187,052.

Many of the patents in addition to disclosing catalysts which may be employed, disclose other process improvements for the catalytic cleavage of aralkyl hydroperoxides to produce phenolic compounds. Such improvements are directed to the ends of increasing yield and purity of the phenols produced by this catalytic cleavage of the aralkyl hydroperoxides. The improvements comprise such things as composition of the reaction medium; use of various solvent systems; methods of addition of the reactants to the reaction vessel, and methods of carrying out batch and continuous reactions. These methods of cleaving aralkyl hydroperoxide involve a cleavage reactor which is equipped with a mechanical agitator and a heat exchange means. The heat exchange means is designed to remove the excess heat of reaction and thereby control the reaction temperature. The mechanical agitator ensures contact of the hydroperoxide and catalyst, thus contributing to a relatively complete cleavage reaction. Examples of this type of cleavage reaction, including the equipment used, are given in the following U.S. Pat. Nos.: 3,376,352; 2,663,735; 3,187,052; 3,626,281; and 2,748,172.

The aralkyl hydroperoxides utilized in the acid catalyzed cleavage to form phenols are commonly the products of a direct oxidation of aralkyl hydrocarbons with molecular oxygen. The aralkyl hydroperoxides produced by direct oxidation contain impurities such as unreacted aralkyl hydrocarbon, other oxidation products, water, and alkaline materials.

In the methods where the cleavage catalyst is a strong mineral acid, particularly sulfuric acid, the water and alkaline materials should be substantially removed from the aralkyl hydroperoxide before it is subjected to the cleavage reaction. Water dilutes the acid catalyst and the alkaline materials neutralize the acid catalyst, thus increasing the reaction time and the acid consumption in the cleavage reaction. Water has the additional disadvantage in sulfuric acid catalyzed cleavage reactions that it forms "browning centers" within which highly colored side products are formed. The highly colored side products must be removed so color specifications can be met by the product phenols. In cleavage reactions employing other acid catalysts, such as phosphoric acid for instance, water is not the problem it is in the sulfuric acid systems. The alkaline materials are a problem in all the systems, since they neutralize the catalyst.

The cleavage reactions described above, employing mechanical agitation, have substantially complete backmixing of reaction products with reactants. They also have appreciable residence times of from fifteen minutes to over 2 hours. Such backmixing and long residence times contribute to the level of cleavage reaction side products. These side products, resulting from side reactions within the cleavage reaction are numerous. They vary according to the types of hydroperoxides subjected to cleavage, the catalyst used, and the range of impurities present in the hydroperoxide reactant. In the mechanically agitated reactions which have an appreciable residence time these side reactions can contribute sufficient highly colored side products to cause serious purification problems. Examples of the types of side reactions which can occur in the cleavage reaction are: condensation of the carbonyl compound, such as forming mesityl oxide from acetone; formation of olefins, e.g. divinyl benzene etc; formation of isopropanol phenol; reaction of phenolic products with the carbonyl compound; oxidation of the phenols by the hydroperoxides, such as formation of quinones from hydroquinones; reaction of quinones with hydroquinone to form quinhydrone; and condensation of olefins to form polymers. There are many other side reactions depending upon the reactants present in the cleavage reaction. Many of the side products so formed are highly colored and must be substantially completely removed for the product phenols to meet the color specifications. The patent literature discloses many methods of removing side products and purifying the phenols. For example see U.S. Pat. Nos.: 3,376,352; 3,187,052; 3,043,883; 2,748,172; 2,663,735; 3,140,318; 3,155,734. The purification of phenol products, however, is increasingly difficult at higher concentrations of side products.

Methods have also been devised for avoiding some of the problems associated with such side reactions. These methods generally limit the choice of operating conditions for the cleavage reaction as by determining what solvents or which catalysts may be used. Also, these methods do not have general applicability to cleavage reactions to produce mono and polyhydric phenols, but are limited to particular reactants.

There is a danger of runaway heats of reaction in the backmixed cleavage reaction vessels. The rate of heat release from the cleavage reaction is controlled, under normal conditions, by the rate of hydroperoxide addition. However, various operating condition changes may cause the concentration of hydroperoxide in the cleavage zone to rise to the point where the rate of hydroperoxide addition no longer controls the heat release. Such operating condition changes as acid failure, excess water, excess alkali, and others can cause the hydroperoxide concentration in the cleavage reaction vessel to rise above normal levels. When normal operating conditions are restored, abnormal amounts of heat will be liberated due to the excessive amount of hydroperoxide present in the reaction medium. Unless the heat exchange means is sufficiently large, the vessel temperature will rise causing the cleavage reaction to speed up, thus producing heat at a greater rate, and so on in a cascading fashion. Under these conditions the temperatures and pressures in the cleavage reaction vessel quickly become uncontrollable. The potential hazard to personnel and equipment from such a runaway reaction is apparent.

The prior art indicates that hydroperoxide rearrangement product quality is improved at higher product to reactant ratios in the reaction mixture, and hence continuous, stirred reactors are indicated as preferable for rearranging hydroperoxides to their corresponding phenolic compounds. It has been found, however, as a result of the present invention that product quality can be improved by limiting the contact between the product and the reactants.

An object of the invention is to provide an improved method for the continuous acid catalyzed cleavage of aralkyl hydroperoxides to produce phenols and carbonyl compounds.

Another object of this invention is to provide a method for the continuous acid catalyzed cleavage of aralkyl hydroperoxides to produce phenols and carbonyl compounds wherein the unwanted side reactions associated with the cleavage reaction are held to a minimum.

A further object of the invention is to provide a method for the continuous acid catalyzed cleavage of aralkyl hydroperoxides to produce phenols and carbonyl compounds which may be controlled by varying the reaction variables of temperature, pressure, catalyst concentration and residence time in the reaction zone.

A further object of the invention is to provide a method for continuous acid catalyzed cleavage of aralkyl hydroperoxides which will produce a phenol product of improved purity.

A further object of the invention is to provide a method for the continuous acid catalyzed cleavage of aralkyl hydroperoxides wherein the danger of injury to personnel and equipment occurring during a runaway reaction is greatly minimized or substantially eliminated.

A further object of this invention is to provide a unique reaction chamber wherein the objects above may be realized in relation to the continuous acid catalyzed cleavage of an aralkyl hydroperoxide to produce phenols and carbonyl compounds.

Other objects and a more complete understanding of the present invention may be realized from the following specification and claims when taken in conjunction with the drawing.

SUMMARY OF INVENTION

According to the present invention a novel method is provided for continuously cleaving aralkyl hydroperoxides in the presence of acid catalyst to produce phenols and carbonyl compounds with a minimum of side product formation and a minimum danger of injury to personnel and equipment resulting from runaway reactions. Such reaction is carried out within a reaction chamber designed to limit the total reaction time to less than the time required for formation of objectionable side reaction products.

The method for cleaving the aralkyl hydroperoxides disclosed herein comprises bringing the aralkyl hydroperoxide into contact with the acid catalyst in the presence of one or more liquid solvents or carrying agents and allowing the cleavage reaction to take place under controlled temperature and pressure conditions in such manner that there is not sufficient hold back of the reaction mixture in the reaction zone to form objectionable side reaction products. The reaction is continued for a time such that substantially all the hydroperoxide is cleaved to the phenol and carbonyl compound but short enough duration that substantial side reactions will not occur. The hazards arising from runaway reactions are diminished by the fact that only small amounts of reactants are present in the reaction chamber, and by the fact that hold back is minimized. Thus, the quantity and concentration of hydroperoxide does not build up to high levels.

The characteristic of a reaction system which is referred to as hold back, is equal to the fraction of a reaction zone which is occupied by reaction mixture fluid which has been in the reaction zone longer than the average residence time. The average residence time is the reaction zone volume divided by reaction mixture flow rate, all in consistent units. This hold back concept arises from the fact that in most continuous flow reactions (except an ideal plug flow reaction) some elements of reaction mixture fluid spend more, others less, than the average residence time in the reaction zone. In a discussion of this concept by Danckwerts (P. V. Danckwerts, Continuous Flow Systems, Distribution of Residence Time, "Chemical Engineering Science, Genie Chemique," pp 1-13, Vol. 2, No. 1, February 1953), incorporated herein by reference, values of hold back for various systems have been calculated as follows:

| Reaction System | Hold Back Value |
| --- | --- |
| Ideal Plug flow | 0 |
| Pipe-turbulent flow | <$\frac{1}{4}$ |
| Pipe-laminar flow | $\frac{1}{4}$ |
| perfectly mixed reactor | 1/e (e-natural function 2.718) |
| Reactor with spaces of non flow (dead spaces) | Approaches the limit of 1 |

Generally, mechanical agitated reactors of the type usually used for cleaving hydroperoxides will have a hold back value between about 1/e and 1, depending upon the degree of mixing achieved therein. It is well known that the output of a chemical reactor will usually be greatest when the hold back is least (except for some auto catalytic reactions). However, we have experienced an unexpected benefit from decreasing the hold back. When the hold back in the cleavage reaction is less than 1/e and preferably about $\frac{1}{4}$ or less, there is a substantial decrease in the amount of highly colored side reaction products which are difficult to remove from the phenolic cleavage reaction products. This result was unexpected since it was assumed that if the efficiency of one reaction (the cleavage reaction) was increased, then the efficiency of other reactions (consecutive) would likewise increase.

This method of cleaving hydroperoxides is made possible by employing a unique reaction system. According to one embodiment of my present invention, an elongated tubular reactor is fitted at one end with means for adding hydroperoxides, acid catalyst, and solvents or carrying mediums and fitted at the other end with a pressure control means and a means for withdrawing the cleavage reaction products. The reactor is provided with a temperature control means whereby the heat of reaction of the cleavage reaction may be removed. This temperature control means may be any adequate temperature control device, such as a constant temperature bath, etc. Such a tubular reactor has a hold back value of about ¼ or less, depending on the flow conditions within the reactor.

The reactor must be designed with the expected capacity in mind. In the tubular reactor embodiment, ratio of reactor length to diameter should be such that adequate reaction time is provided for the cleavage of substantially all the hydroperoxide present. Flow rates through the reactor may be varied over rather broad limits by varying the reaction conditions of temperature, pressure, and ratio of carrying agent to hydroperoxide.

Although the discussion of this invention is in terms of employing a tubular reactor, we do not propose to limit our invention to tubular reactors. Other reactor systems possessing hold back values of less than 1/e will be obvious to those skilled in the art. We include in our invention any such reactor system which possess hold back values of less than 1/e, particularly those with hold back values of about ¼ or less and which provide an average residence time of about 3 to 9 minutes. Examples of other reactor systems which can be constructed to possess the necessary low hold back values are: (1) Shell and tube configuration, where the reaction mixture flows through a set of tubes into a channel head and into another set of tubes; (2) a reactor system employing mechanical agitation wherein the volume of the reaction zone influenced by the mechanical agitation is small compared to the total reaction volume. Other reaction systems possessing the necessary characteristics will occur to those skilled in the art of reactor design.

DETAILED DESCRIPTION OF THE INVENTION

Figure 1:
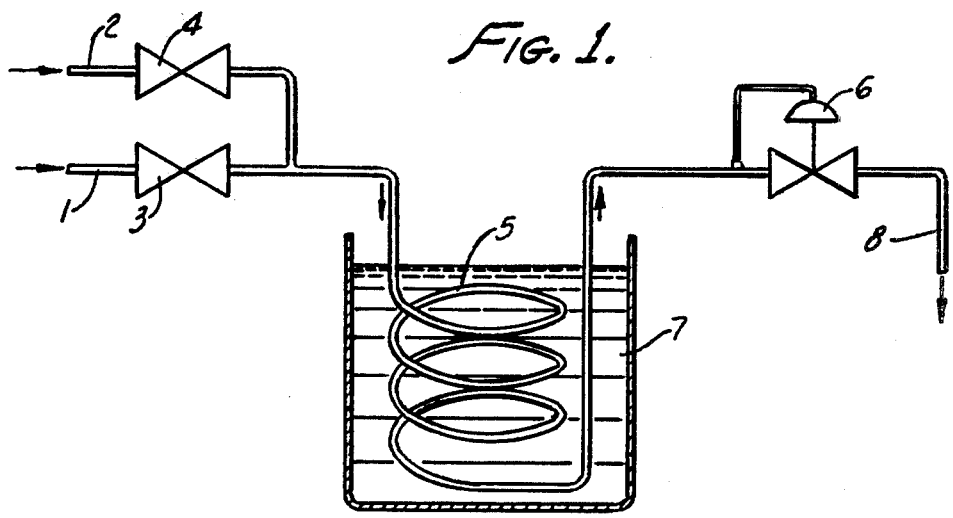
FIG. 1, is a diagrammatic representation of the process of my present invention employing a tubular reactor. The hydroperoxide, dissolved in a solvent or suspended in a liquid carrying agent is brought to the tubular reactor (5) through line (1). The rate of addition of hydroperoxide is controlled by valve (3). The acid catalyst, whether pure catalyst, dissolved in a solvent, or suspended in a carrying agent, is brought to the tubular reactor (5) through line (2). The catalyst flow is controlled by valve (4). The acid catalyst, hydroperoxide and carrying agent is brought into turbulent contact within the tubular reactor (5), where the temperature is controlled by the constant temperature bath (7), the pressure is controlled by pressure controller (6) and residence time of reactants is determined by the total flow rate and the tubular reactor length. The reaction product is continuously withdrawn through line (8).
Figure 2:
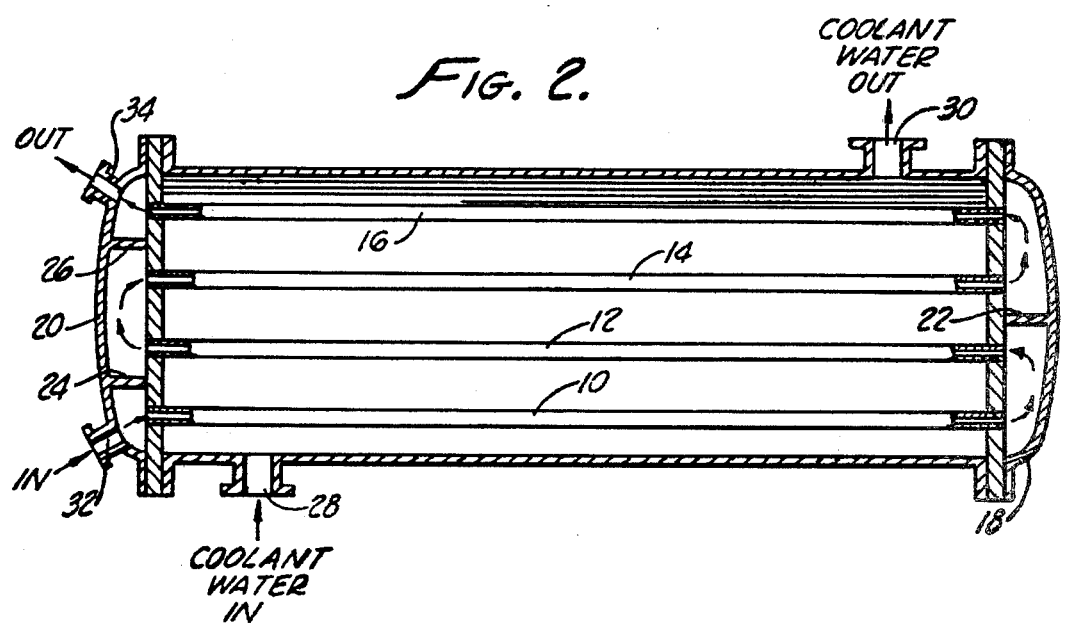
FIG. 2 shows, in cross section, another embodiment of our invention employing a shell and tube configuration in which the reaction mixture flows through a series of tubes 10, 12, 14 and 16. The reaction mixture path is defined at the tube ends by channel head 18 and 20 with baffles 22, 24, and 26. The oxidate feed enters the reactor via inlet 32 and the product exists via inlet 34. Cooling water is circulated exteriorly of the tubes through nozzles 28 and 30.

We have found that side reactions are substantially reduced if the acid catalyzed cleavage of aralkyl hydroperoxides can be accomplished with limited holdback of the reaction mixture in the reaction zone. Since many of the side reactions occur at a rate slower than the cleavage reaction rate, the side reactions can be further minimized by reducing the total reaction time to approximately that time required to cleave substantially all the hydroperoxide. Also, since there is a danger of runaway reaction if the dihydroperoxide level becomes too high, it is desirable to have a reactor system of limited volume to decrease the chance of injury resulting from such a runaway reaction.

The elongated tubular reactor disclosed here provides one means whereby the improved method of cleaving the aralkyl hydroperoxides can be performed.

According to our improved method, many aralkyl hydroperoxides may be cleaved to form the corresponding phenols and carbonyls. For instance:

| Hydroperoxide | Phenol | Carbonyl |
|---|---|---|
| Cumene hydroperoxide | phenol | acetone |
| p-diisopropylbenzene dihydroperoxide | hydroquinone | acetone |
| m-diisopropylbenzene dihydroperoxide | resorcinol | acetone |
| sec-butylbenzene hydroperoxide | phenol | MEK (methyl ethyl ketone) |
| p-sec-butylbenzene dihydroperoxide | hydroquinone | MEK |
| m-sec-butylbenzene dihydroperoxide | resorcinol | MEK |
| 1,3,5 triisopropylbenzene trihydroperoxide | 1,3,5 tri hydrobenzene | acetone |

Any other compound of the formula

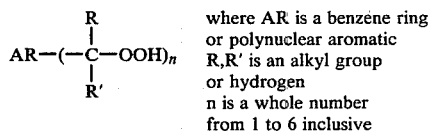

where AR is a benzene ring or polynuclear aromatic
R,R' is an alkyl group or hydrogen
n is a whole number from 1 to 6 inclusive may likewise be cleaved to form the corresponding phenol and carbon compound.

Our method for cleaving aralkyl hydroperoxides allows a flexibility of operating conditions, without a sacrifice of product quality, which is impossible employing the prior methods of hydroperoxide cleavage.

Many different acid acting catalyst may be employed, such as sulfuric acid, other strong mineral acids, $SO_2$, phospheric acid, Lewis Acids such as aluminum chloride and other Friedel-Crafts catalysts and boron trifluoride, acid acting synthetic resins, acid acting inorganic oxides such as silica-alumina cracking catalyst, etc. The catalyst may be liquid, solid or vapor. The catalyst may be added alone, dissolved in a solvent or suspended in a liquid carrying agent.

The hydroperoxide, if liquid, may be added alone, in solution with a solvent, or suspended in a carrying agent. If the hydroperoxide is added alone, then additional solvent or carrying agent must be added to carry the reaction products through the reactor. The hydroperoxide, if a solid, may be added in solution with a solvent or suspended in a carrying agent.

One or more solvents and/or carrying agents may be added. It is sometime useful to add a liquid within which the reaction product is soluble and also a liquid (immiscible with the first) which is a solvent for the side reaction products. This method of two solvents aids in the subsequent purification of the phenolic product, and it may be practiced to good advantage within our process. If it is not desired to employ two solvents, it is not necessary, since by following our method the amount of side reaction products is substantially decreased.

Further flexibility of operation is allowed in our process by temperature control. The reaction temperature may be adjusted by varying the temperature of the heat exchange medium which surrounds the reactor and which carries away the excess heat of reaction. The reaction temperature is preferably maintained between about 50° and 120° C.

The pressure is easily controlled to ensure that no vaporization occurs within the reaction chamber.

Our improved method of cleaving aralkyl hydroperoxide in the presence of an acid catalyst to form phenols and carbonyl compounds is described as follows:

The aralkyl hydroperoxide is prepared for continuous injection at a steady rate into the cleavage reactor. The hydroperoxide is first freed of any water and solid alkaline materials which will interfere with the acid catalyzed reaction. The water may be substantially removed by azeotropic distillation with a hydrocarbon such as benzene (see Co-pending application No. 985 for this method of removing water). A convenient way of removing the solid alkaline material is to dissolve the hydroperoxide in an organic solvent, such as acetone, and subsequently filter out the insoluble alkaline materials. The water and alkaline materials may be left in the hydroperoxide charged to the reactor, but they affect the catalyst activity so it is better to remove both water and alkaline material.

The hydroperoxide, free of water and alkaline material is then sent to the cleavage reactor charge. This hydroperoxide may be fed to the cleavage reactor undiluted, dissolved in a solvent or suspended in a liquid carrying agent. The most convenient way to add the hydroperoxide is in solution with an organic solvent such as the carbonyl product of the cleavage reaction. The charge rate of hydroperoxide can be controlled very easily in this manner, and introduction of an extraneous substance is avoided since the carbonyl compound is also produced in the cleavage reaction. The solvent is present preferably in an amount of about 3:1 to 20:1 of solvent to hydroperoxide.

The acid catalyst is then prepared for continuous charge to the cleavage reactor. The catalyst must be fed at a carefully controlled rate to ensure a catalytic amount is present and at the same time avoid too large an excess. The acid catalyst must be neutralized or removed at the end of the cleavage reaction, and large excesses of acid catalyst make neutralization and/or removal difficult. The acid catalyst should be present in an amount of at least about 0.10% of the reaction mixture, generally about 0.1 to 5%, preferably about 0.10 to 1.0%. At higher acid concentrations the acid tends to act as a polymerization catalyst to form undesirable and objectionable by-products.

It is convenient to employ an acid catalyst which is a liquid or a vapor, but a solid catalyst may be employed if sufficient care is taken that the rates of addition and removal are closely maintained. As the volumes of catalyst added are relatively small it is convenient to dilute a liquid catalyst with an inert solvent. This makes control of the rate of catalyst addition simpler.

In accordance with the embodiment of my present invention which utilizes a tubular reactor for cleavage of an aralkyl hydroperoxide, the hold back value of the reaction mixture is about $\frac{1}{4}$ or less, depending upon the flow conditions within the reactor.

The hydroperoxide is fed into the feed end of an elongated tubular reactor at a steady rate and the acid catalyst is added near the same end. Sufficient solvent or carrying agent must be present to distribute the heat of reaction to the tubular reactor wall where this heat can be removed by transfer to the heat transfer medium surrounding the tubular reactor. The solvent system may consist of one or more solvents.

After hydroperoxide, acid catalyst and solvent and/or carrying agent flow is established, the temperature within the reactor is adjusted to the desired reaction temperature. This is conveniently done by adjusting the temperature of the heat transfer medium surrounding the tubular reactor. The total flow through the reactor must proceed at a velocity sufficient to ensure contact of the hydroperoxide and acid catalyst. Good contact is necessary for complete cleavage of the hydroperoxide.

The length and diameter of the tubular reactor must be preselected with the total flow rate in mind. The reactor length, at the preselected flow rate and reactor diameter, will determine the residence time within the reactor. The residence time must be sufficient to allow substantially complete cleavage of the hydroperoxide but not much greater than that. Increased residence time under reaction conditions contributes to unwanted side product formation. Generally, a residence time of about 1 to 15 minutes is satisfactory for a tubular reactor, with the preferred range being about 5 to 12 minutes.

Effective residence time can be varied, if the reactor length is preset, by varying the total flow rate. The same hydroperoxide rate may be maintained by varying the hydroperoxide/solvent or carrying agent ratio. Further adjustments of the rate of reaction may be made by varying the reaction temperature. Thus, the method disclosed here has substantial flexibility.

A back pressure control device should be employed on the discharge end of the tubular reactor. This is to prevent any substantial vaporization within the tubular reactor. Although some vaporization does no harm, so long as solid materials do not precipitate and plug the reactor, the vapor formed will act to reduce the effective volume of the tubular reactor. This reduced volume acts the same as a reduction of the residence time. Care must be taken that the generation of vapor does not force the reactants through the reactor faster than the cleavage reaction can proceed to substantial completion.

The reaction effluent is removed from the discharge end of the tubular reactor after the pressure control means. From this discharge the reaction effluent is sent to further processing for product recovery and purification.

This method of cleaving aralkyl hydroperoxides to form phenols and carbonyl compounds has many manifestations depending upon the actual hydroperoxide—acid catalyst—solvent and/or carrying agent system employed. The actual operating parameters of temperature, pressure, residence time, catalyst concentration and volume of solvent and/or carrying agent per volume of reactants will depend upon the system chosen.

Some of the operating conditions are interdependent, for instance, lower temperature may be used if a longer residence time is allowed. The following examples demonstrates specific embodiments of the invention, showing proportions of reactants, residence times, pressures and temperatures for the specific systems employed. It must be understood that the examples here are given only to demonstrate the practical utilization of our invention and should not be construed as limiting the scope of the present invention.

EXAMPLE I

A solid hydroperoxide containing cake, recovered by filtration from the reaction mixture obtained from the oxidation of para-diisopropylbenzene with molecular oxygen in the presence of aqueous sodium carbonate, was treated in the following manner to recover a solid product rich in p-diisopropylbenzene dihydroperoxide. Fifty pounds of the solid cake was slurried with 150 pounds of benzene at room temperature and the slurry filtered. This filter cake was slurried with 150 pounds of benzene at room temperature and the slurry filtered. Finally the remaining solids were slurried with 150 pounds of hexane and this slurry filtered. The solids recovered from the hexane slurry were dried, then analyzed and were found to contain 76.5 wt. % hydroperoxide (calculated as p-diisopropylbenzene dihydroperoxide) and 23.7 wt. % p-(2-hydroxy-2 propyl) α,α dimethyl-benzyl hydroperoxide and traces of other oxidation products. The ratio of diisopropylbenzene monohydroperoxide to diisopropylbenzene dihydroperoxide was determined to be 0.19/1. This crude hydroperoxide was dissolved in sufficient acetone to produce a solution containing 20 wt. % p-diisopropylbenzene dehydroperoxide. The solution was filtered to remove any remaining sodium carbonate and was passed through a tube containing 5A molecular sieve to remove water. This treated solution was then used as feed to a continuous cleavage reaction employing a tubular reactor.

The tubular reactor system used in this experiment consisted of two graduated cylinders with bottom stop cocks which were used as feed tanks, one for the hydroperoxide-acetone solution and one for the catalyst. The hydroperoxide-acetone solution was passed via $\frac{1}{4}''$ stainless steel tubing, to one side of a double head metering pump. The acid catalyst was passed to the other side of the pump. At the pump discharge the streams were brought together at a tee and the combined stream was passed into a 20' coil of $\frac{1}{4}''$ stainless steel tubing which comprised the tubular reactor. This tubular reactor was immersed in a heated water bath. At the discharge of the tubular reactor a cross was installed, one branch of which held a pressure gauge. Another branch provided the sensing point for the pressure control instrument and the final branch provided the passage for the reaction effluent from the tubular reactor. The reaction effluent leaving the tubular reactor was passed into a straight section of $\frac{1}{4}''$ stainless steel tubing. This tubing was wrapped with $\frac{1}{4}''$ aluminum tubing through which chilled water was passed. The reactor effluent was thus cooled to about 25° C. within the straight section of tubing. At the discharge of the straight section of tubing a back pressure control valve was installed. This valve, controlled by the pressure control instrument, was used to control the tubular reactor outlet pressure. The reaction effluent was discharged from the pressure control valve into a receiving vessel.

A series of experimental runs was made employing the hydroperoxide material and the tubular reactor described above. The data collected during this series of experiments is tabulated in the following tables. The flow rate of the reaction mixture through the tubular reactor was maintained at all times in the laminar flow region, thus the hold back value was about $\frac{1}{4}$.

Table I

| EFFECT OF RESIDENCE TIME ON CONVERSION[1] | |
|---|---|
| Residence Time (minutes) | % Conversion (hydroperoxide disappearance) |
| 0.92 | 60.27 |
| 1.31 | 64.17 |
| 2.0 | 77.06 |
| 3.0 | 88.16 |
| 5.0 | 97.40 |
| 6.0 | 98.50 |
| 7.0 | 99.50 |
| 8.0 | 99.50 |

[1] At 90° C. reaction temperature, 30 psig and 0.2% $H_2SO_4$

Table II

| EFFECT OF TEMPERATURE ON CONVERSION[2] | |
|---|---|
| Temperature °C. | % Conversion (hydroperoxide disappearance) |
| 60 | 90.63 |
| 70 | 94.39 |
| 75 | 94.92 |
| 80 | 95.44 |
| 85 | 95.70 |
| 90 | 99.48 |
| 95 | 99.74 |

[2] At seven minutes residence time, 30 psig and 0.2% $H_2SO_4$

Table III

| EFFECT OF ACID CONCENTRATION ON CONVERSION[3] | |
|---|---|
| $H_2SO_4$ Wt. % | % Conversion (hydroperoxide disappearance) |
| 0.2 | 99.5 |
| 0.15 | 97.4 |
| 0.10 | 96.4 |
| 0.05 | 49.5 |

[3] At 90° C., 30 psig and seven minutes residence time.

Samples from these runs were light amber color. The samples were treated with $CaCO_3$ to neutralize the acid catalyst, then filtered to remove insoluble materials. The filtered solution was mixed with an equal weight of toluene and this mixture was subjected to a distillation step to remove acetone. Upon cooling, hydroquinone precipitated as off white crystals from the toluene mixture which remained in the bottom of the distillation flask. This hydroquinone was analyzed as being 99.3% pure and represented 97.3% of the theoretical amount of hydroquinone, based upon diisopropylbenzene dihydroperoxide fed to the tubular reactor. The toluene contained substantially all the other reaction products, including unrecovered hydroquinone, para-isopropyl phenol, and para-2 hydroxy isopropyl phenol.

EXAMPLE II

As a comparative example, a portion of the feed prepared for example I was subject to cleavage in a continuous mechanically agitated reactor. The reactor, a one liter autoclave, was equipped with a stirrer and a pressure regulator. The aforementioned Danckwerts article indicates that the hold back value of such reactor is greater than 1/e. The crude dihydroperoxide dissolved in acetone was fed at a constant rate into the top of the autoclave along with the sulfuric acid catalyst. The liquid level in the autoclave was maintained constant by drawing product solution off the bottom of the autoclave. The temperature of the reaction was maintained by allowing acetone to flash off through the pressure control valve.

The reaction product solution recovered from this reaction varied in color from dark brown to black. The hydroquinone was recovered from this reaction product solution in the same manner as the hydroquinone in example I. The results of this example are as shown in table IV.

TABLE IV

| Run No. | Temp. °C. | % H$_2$SO$_4$ in Feed | Residence Time Minutes | % Hydroperoxide Conversion | HQ Yield % of theor. | HQ % Purity | HQ Color |
|---|---|---|---|---|---|---|---|
| 1 | 90 | 0.1 | 20 | 99 | — | 93.13 | Black |
| 2 | 90 | 0.1 | 20 | 99 | 97 | 86.6 | Black |
| 3 | 90 | 0.2 | 21 | 99 | 105 | 88.5 | Dk.Brow. |
| 4 | 90 | 0.1 | 7 | 99 | 99 | 97.7 | Red-gray |
| 5 | 90 | 0.4 | 9 | 99 | 102 | 99.0 | Tan |
| 6 | 90 | 0.05 | 9 | 99 | 100 | 99.4 | Tan |
| 7 | 90 | 0.025 | 9 | 46 | — | — | — |

From the results of example II, compared to the results of Example I, it can be seen that the hydroperoxide cleavage reaction product is greatly improved by employing the process of our invention compared to the product obtained by practicing the process disclosed in the prior art.

What is claimed is:

1. A continuous process for catalytically cleaving an aralkyl hydroperoxide of the general formula

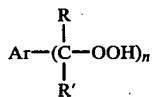

where Ar is an unsubstituted benzene nucleus, alkyl benzene nucleus or polynuclear aromatic, R and R' are alkyl, cycloalkyl or hydrogen, and n is a whole number from one to three inclusive, to form the corresponding phenolic and carbonyl compounds, comprising the steps of:

(a) forming a reaction mixture by continuously combining said hydroperoxide in the presence of a substantially non-reactive material selected from the group consisting of an organic solvent and liquid carrier with an acid cleavage catalyst in an amount of at least about 0.10% of said reaction mixture, said catalyst being selected from the class consisting of mineral acids and Lewis acids, (b) flowing said reaction mixture through a reaction zone characterized by the lack of substantial backmixing at a temperature of about 50° C.–120° C. for a residence time sufficient to complete cleavage of said hydroperoxide to its corresponding phenolic compound, the hold back in said reaction zone being limited to a value less than $\frac{1}{e}$, where e is the natural function 2.718 to control the formation of highly colored side products, and (c) continuously recovering from said reaction zone a reaction effluent containing said cleavage products and substantially devoid of highly colored side products.

2. A process of claim 1 wherein said reaction is performed in an elongated tubular reactor.

3. The process of claim 2 wherein said reactor has a volume cpacity such that the flow rate of said hydroperoxide and catalyst there through has a reaction residence time of about 5 to about 12 minutes.

4. A process of claim 1 wherein the ratio of said solvent to said hydroperoxide is about 3:1 to 20:1.

5. The process of claim 1 wherein said rearrangement catalyst is present in an amount of about 0.10 to 5.0% of the said reaction mixture.

6. The process of claim 1 wherein said rearrangement catalyst is present in an amount of about 0.10 to 1.0% of said reaction mixture.

7. The process of claim 1 wherein the hold back valve of the reaction mixture is about $\frac{1}{4}$ or less.

8. The process of claim 1 wherein said organic solvent comprises the carbonyl product of the cleavage reaction.

* * * * *